United States Patent [19]

Herrick

[11] Patent Number: 5,782,911
[45] Date of Patent: Jul. 21, 1998

[54] ARTIFICIAL LENS INCLUDING A MULTIFOCAL LENS SYSTEM HAVING ECCENTRIC AXIS AND METHOD

[75] Inventor: Robert S. Herrick, Rialto, Calif.

[73] Assignee: Herrick Family Limited Partnership, a Calif Ltd Part., Ranch Cucamonga, Calif.

[21] Appl. No.: 853,743

[22] Filed: May 9, 1997

Related U.S. Application Data

[63] Continuation of Ser. No. 352,381, Dec. 8, 1994, abandoned.
[51] Int. Cl.$^6$ .................. A61F 2/14; A61F 2/16
[52] U.S. Cl. ............ 623/5; 623/6; 351/161
[58] Field of Search ............ 623/5, 6; 351/159, 351/160 R, 161

[56] References Cited

U.S. PATENT DOCUMENTS

| | | | |
|---|---|---|---|
| 4,330,169 | 5/1982 | Kantor | 351/159 X |
| 4,648,878 | 3/1987 | Kelman | 623/6 |
| 4,666,446 | 5/1987 | Koziol et al. | 623/6 |
| 4,906,245 | 3/1990 | Grendahl | 623/6 |
| 5,178,636 | 1/1993 | Silberman | 623/6 |

Primary Examiner—Mary Beth Jones
Attorney, Agent, or Firm—Daniel J. Meaney, Jr.

[57] ABSTRACT

An artificial lens adapted for use in an eye having a macula is shown. The artificial lens is adapted to be affixed to an eye and has a multifocal optical lens system wherein the principal axis of each lens is eccentric to each other for directing light rays from each image of each lens of the multifocal optical lens system onto a macula of an eye. In the preferred embodiment, the artificial lens includes a first lens having a predetermined diopter power for receiving light rays from a near object and a prism having a preselected diopter power. The prism is positioned on a selected surface of the first lens for directing paracentral light rays from a near object onto a macula of an eye and central light rays to a location superior of the macula. The artificial lens includes a second lens having a predetermined diopter power positioned eccentrically inferior of said first lens for receiving light rays from a distant object and a second prism having a preselected diopter power. The second prism is positioned on a selected surface of the second lens for directing paracentral light rays from a distant object onto a macula of an eye and central light rays to a location inferior of the macula. A method for producing multiple images of an object for an eye is also shown.

26 Claims, 5 Drawing Sheets

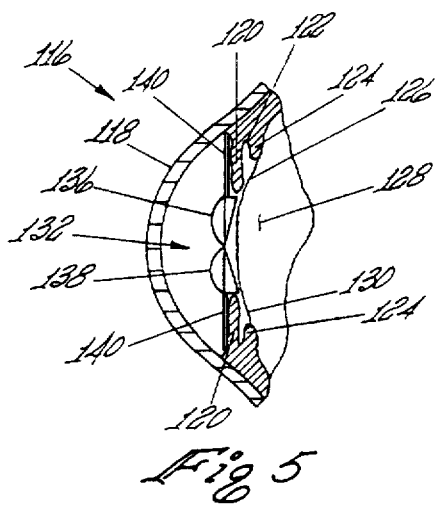
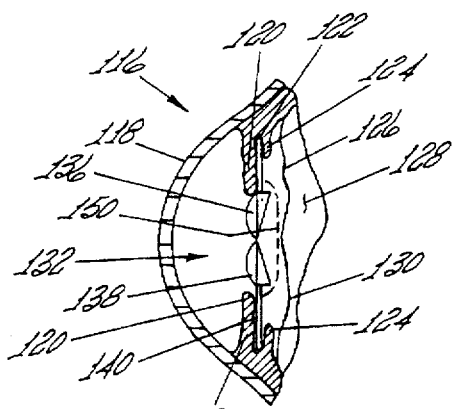
Fig 5
Fig 6
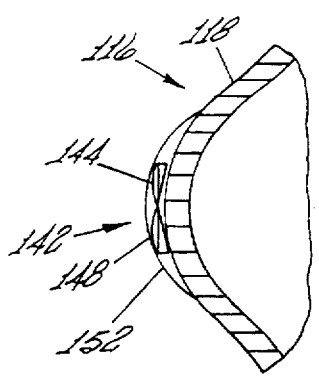
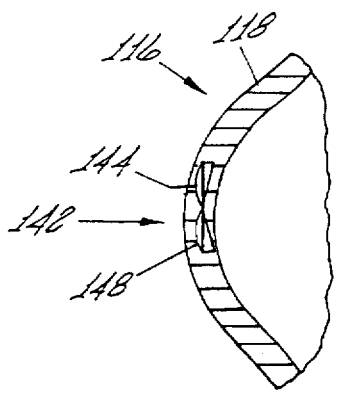
Fig 7
Fig 8
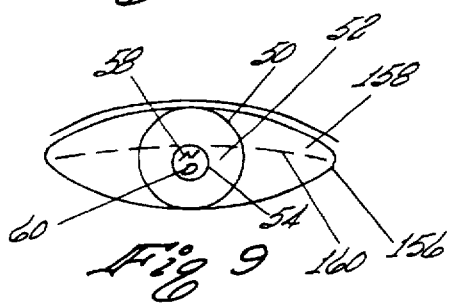
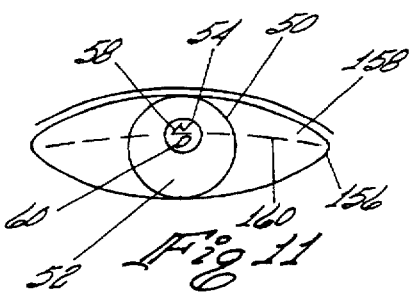
Fig 9
Fig 11
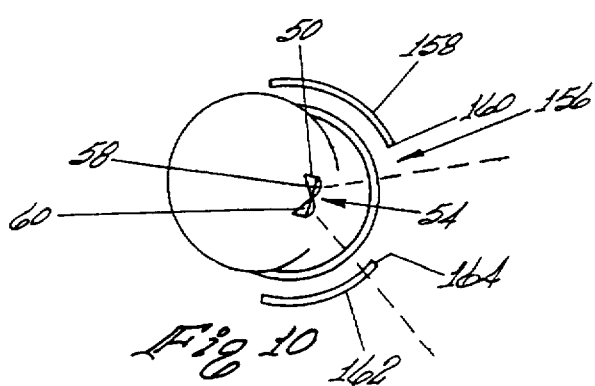
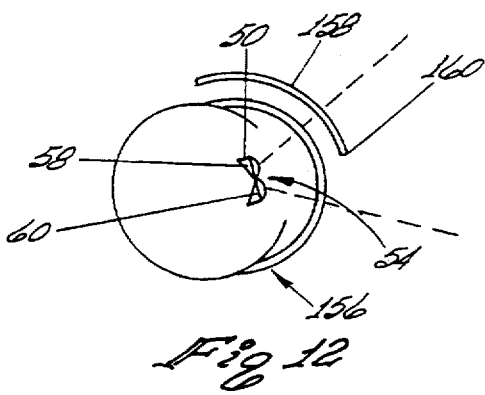
Fig 10
Fig 12

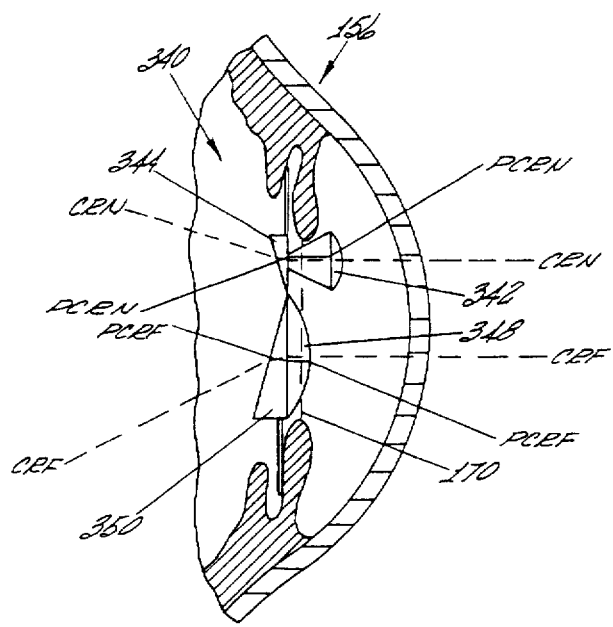
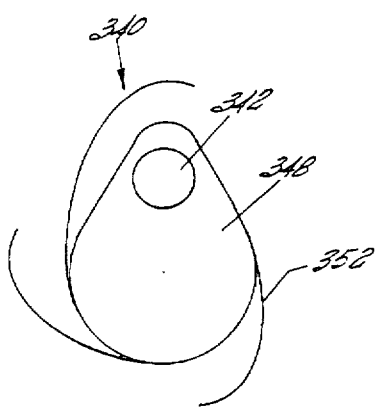
Fig 21
Fig 20
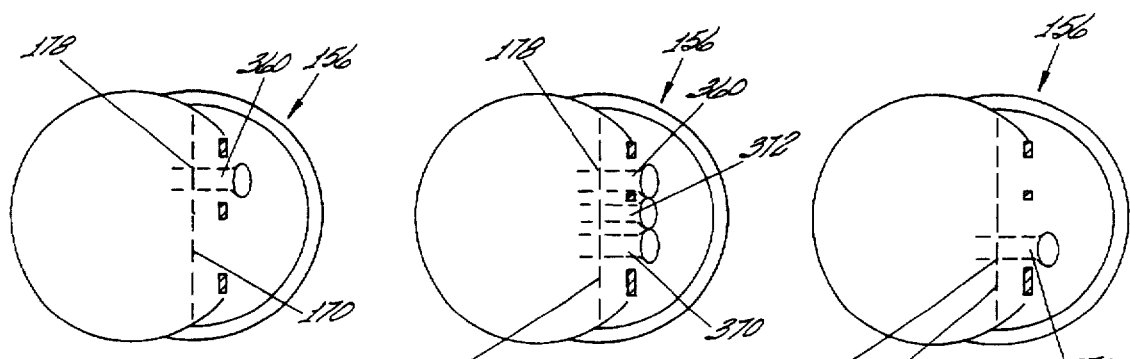
Fig 22a　　　Fig 22b　　　Fig 22c

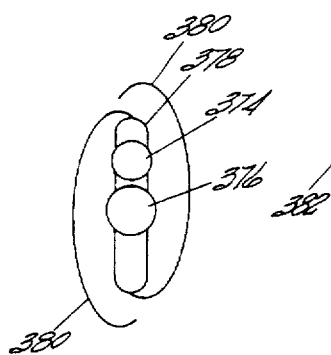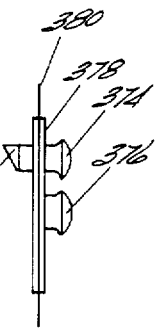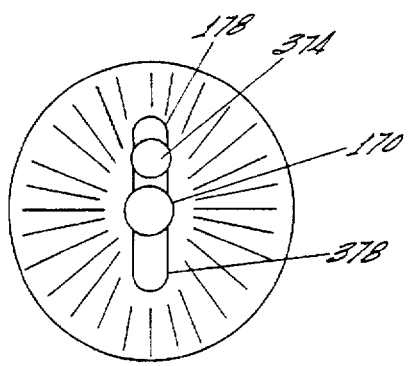
Fig 23  Fig 24  Fig 25
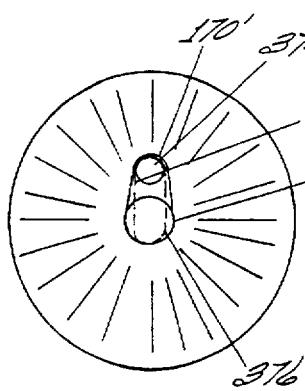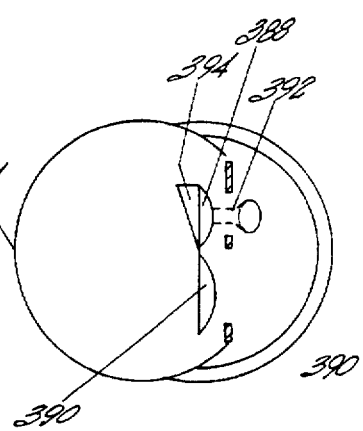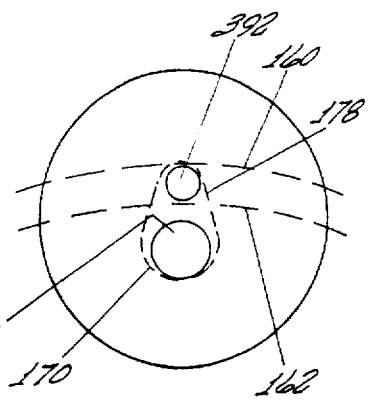
Fig 26  Fig 27  Fig 28
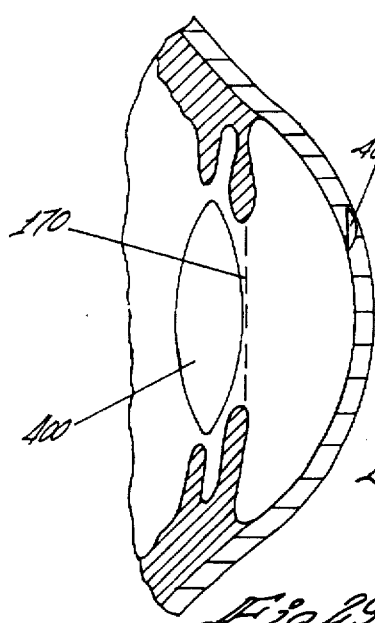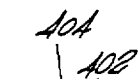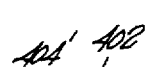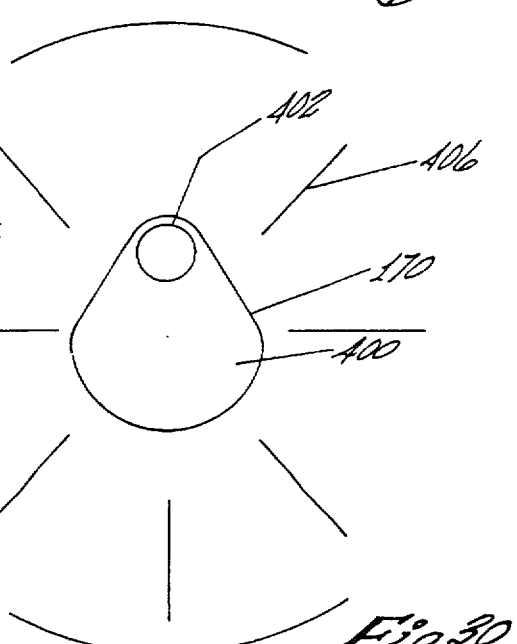
Fig 29b
Fig 29c
Fig 29a  Fig 30

ARTIFICIAL LENS INCLUDING A MULTIFOCAL LENS SYSTEM HAVING ECCENTRIC AXIS AND METHOD

This application is a continuation, of application Ser. No. 08/352,381, filed Dec. 4, 1994, now abandoned.

BACKGROUND OF THE INVENTION

1. Field of the Invention

This invention relates to the field of ophthalmic optics and artificial lens adapted to be affixed to an eye and more specifically relates to an artificial lens adapted to be located in an eye having a macula wherein the artificial lens comprises a multifocal optical lens system wherein each principal axis is eccentric to each other for directing light rays from each image of each lens onto the macula of an eye. In the preferred embodiment a first lens system having a prism directs paracentral light rays from a near object onto the macula and a second lens system having a prism positioned in a cooperating relationship to the first lens system directs central light rays from a distant object onto the macula of an eye.

This invention also relates to method for producing multiple images of an object for an eye using a multifocal optical lens system wherein the principal axis of each lens system is eccentric to each other.

2. Description of the Prior Art

It is known in the art that when the optical power of the natural eye is emmetropic, the eye is naturally focused for distance with the ciliary body at rest. The natural eye has the ability to change (increase or decrease) the converging power of the natural (crystalline) lens for near vision and for intermediate vision, that is vision in the range of about 10" to about 18" or 20".

With aging, the eye's natural (crystalline) lens loses its ability to adequately increase its converging power. In order to provide for a sharp focus near vision, it is known in the art to make use of artificial lens system. It is also known in the art to utilize a plurality of artificial lens systems such as glasses or spectacles, contact lens, intraocular lens, corneal lens and intracorneal lens, all of which are utilized to produce a focused near vision. Such lens systems are designed to use concentric lens system for distant and near images and the images are passed through the natural round pupil as the only entrance of light to the retina.

Glasses and spectacles are well known in the art and are selected to have a diopter power to produce the correction required to focus near vision. Also, it is known in the art that such glasses or spectacles comprise bifocal lens for near and distant vision correction or trifocal glasses for near, intermediate and distant correction vision, all of which have concentric principal axes.

Contact lens likewise are well known in the art. Typical of the known prior art which describes contact lens are U.S. Pat. No. 3,034,403 relating to a contact lens of apparent variable light absorption characteristics; U.S. Pat. No. 3,270,099 which relates to a method for making multi-focal length, concentric contact lens and U.S. Pat. No. 4,402,579 which discloses and teaches various concentric axes contact lens structures.

Typically, contact lens are positioned over the anterior surface of the pupil. The natural crystalline lens and iris remain in place and perform their natural functions and cooperate with the contact lens to focus the appropriate images on the macula.

It is also known in the art to utilize prisms in glasses and spectacles both located along the same axis to improve the image focused on the natural crystalline lens.

It is also known in the art to utilize intraocular lens to replace the natural crystalline lens in a cataracts operation. Intraocular lens are implanted into either the anterior chamber or posterior chamber of the eye and are utilized in place of the natural crystalline lens. Typical of such intraocular lens are U.S. Pat. Nos. 4,010,496 which discloses a bifocal lens which is positioned within the anterior chamber; U.S. Pat. No. 4,244,060 which discloses an intraocular lens having a lens body and a plurality of lens-centering filaments extending outwardly in a common plane from spaced rim portions of the lens body; U.S. Pat. No. 4,485,499 which discloses intraocular posterior chamber lens and U.S. Pat. No. 4,976,732 which discloses an optical lens wherein the lens body has integral therewith a predetermined area which is adapted to selectively intercept and pass light through the lens body in a manner to obtain an optical effect for substitution of the loss of accommodation of a phakic, aphakic and pseudophakic eye.

U.S. Pat. No. 4,994,080 discloses an optical lens having stenopaeic openings located in the central area thereof which produces parallel light transmitting paths for passing light rays along a path defining the visual axis of the eye and forwarded onto the fovea centralis in a manner to obtain an optical effect by increasing the depth of focus of the eye in order to substitute for the loss of at least one of the focusing power and the accommodation of the eye.

Artificial lens are also known in the art which are capable of being implanted into the cornea of an eye and which become encapsulated by growth of the corneal epithelium of the cornea of the eye over the anterior surface of lens implanting the same. One such artificial lens fabricated from a collagen-hydrogel material is disclosed in U.S. Pat. No. 5,112,350.

The natural (crystalline) lens degrades as the age of an individual approaches the 40-to-50-year-age range such that the natural lens can no longer adequately change shape due to a loss of elas ticity of the lens of the eye causing defective accommodation and inability to focus sharply for near vision. This condition is referred to as a presbyopia.

When this occurs, an individual requires additional converging power (plus) for near vision. This is commonly supplied by the lower lens in a bifocal artificial lens. As the individual approaches the age range of 65-to-70-years, substantially all of the natural converging powers of the lens is lost and additional convergence for near requirement must be made stronger. In such instances, the bifocal lens of the glasses, contact lens or artificial lens must supply all the convergence of light for near vision.

Following cataract extraction and intraocular lens implantation, there remains the need for additional convergence of light for near vision. With monofocal intraocular lens ("IOL") focused for distance, the near vision convergence must be completely supplied by the bifocal glasses or a single vision reading glasses.

Multiple lens IOLs are known in the art and typically create multiple light rays which are directed on the macula. The artificial lens disclosed in U.S. Pat. Nos. 3,034,403 and 4,976,732 described above produce multiple light rays for the eye. Typically, the multiple lens IOLs do not have provisions for restricting the light from near and far and spontaneously flood the macula with excess light. Also, light passing through multiple lens IOLs enters the eye through each of the optical systems resulting in both a sharp image and a blurred image of the same image impinging upon the macula. This results in: (a) loss of color purity; (b) loss of contrast; and (c) inability of the retina to adapt since the brain perceives the flooding and receipt of extraneous light as too much light.

An intraocular lens that functions as a regular intraocular lens and, in tandem with or concentric with a high plus spectacle lens, as a Galilean telescope, was described in an article entitled "The Telescopic Intraocular Lens" by Jeffrey Koziol, M. D., which appeared at pages 43 and 44 of a compilation of papers presented at the Eleventh National Science Writers Seminar in Ophthalmology, Sept. 16–Sept. 19, 1990 at Universal City, Calif. (the "Koziol Reference"). The Koziol Reference describes the telescopic intraocular lens as a teledioptic lens having a peripheral convex and central concave (minus) portion which have concentric axes. A full range of visual field and normal image size is achieved with the teledioptic lens. A magnified image is obtained when an image in a visual field is viewed through the minus portion of the lens and a high-plus spectacle.

SUMMARY OF THE INVENTION

None of the prior art discloses, teaches or suggests an artificial lens system adapted to be affixed to an eye involving the separation of retinal images and directing light rays from both near and far images such that simultaneously different light rays of the same object strike the macula. In the preferred embodiment portions of the light rays are directed to locations superior and inferior to the macula.

The known glasses or spectacles having a prism do not place the prism on a selected surface of a lens to produce and direct disparate images to the macula.

The intraocular lens of the prior art utilized in the eye function to pass light rays of both near and far vision images onto the macula. Under certain light conditions, the macula is flooded with excess light thereby making it more difficult for the brain to interpret the image due to the presence of excess light.

In multiple lens IOLs, numerous light rays are presented to the macula through the multiple optical systems resulting in both a sharp image and a blurred image of the same object. As a result, the retina is unable to adapt to the multiple images since the brain perceives the flooding of extraneous light and the blurred image as additional light making interpretation thereof difficult.

The telescopic intraocular lens of the Koziol Reference requires use with a high plus, concentric spectacle to develop a magnified image.

The present invention relates to a novel, new and unique lens which is in the form of an artificial lens including a multifocal optical lens system having eccentric axes which is affixed to an eye. The lens of the present invention overcomes each of the above problems associated with the prior art while concurrently producing a system for developing specific light rays from near and distant images of objects which are focused on the macula.

The artificial lens of the present invention is adapted for use in an eye and comprises means adapted to be affixed to an eye having multifocal optical lens system wherein the principal axis of each lens is eccentric to each other for directing light rays from each image of each of the multifocal lens onto a macula of an eye. In the preferred embodiment, the artificial lens includes an image producing means comprising a first lens having a predetermined diopter power for receiving a near image and a prism having a preselected diopter power. The prism is positioned on a selected surface of the first lens and directs paracentral light rays from a near object onto the macula of the eye and central light rays of the near object superior of the macula. The artificial lens includes a second lens having a predetermined diopter power positioned eccentrically inferior of the first lens for receiving light rays from a distant object. The second lens includes a second prism having a preselected diopter power. The second prism is positioned on a selected surface of the second lens and directs paracentral light rays from the distant object onto a macula of the eye and central light rays from the distant object inferior of the macula. Also, a method is disclosed herein for producing multiple images for an eye comprising the step of affixing to an eye an artificial lens having a multifocal optical lens system wherein the principal axis of each lens is eccentric to each other for directing light rays from each image of each lens of the multifocal optical lens onto a macula of an eye.

Although it is known in the prior art to utilize prisms in glasses, the prior art does not disclose, teach, suggest utilizing an artificial lens within the eye having a multifocal optical lens system wherein the principal axis of each lens system is eccentric to each other for directing light rays from each image of each lens of the multifocal optical lens system onto a macula of an eye. The artificial lens of the present invention maintains a separation of light rays from images of the two lens systems such that the macula will not be simultaneously presented with a fuzzy image and a clear image of the same object.

Thus, one advantage of the present invention is that the artificial lens system in the preferred embodiment is arranged such that the first lens system located superiorly in the eye, when in use, permits light to pass therethrough onto the macula thereby directing paracentral light rays of a near object onto the macula and central light rays of the same object superior of the fovea onto the macula.

Another advantage of the present invention is that the multifocal optical system provides for near and distant correction of refractive error that does not use glasses or other similar external eye devices.

Another advantage of the present invention is that the two lens system in the multifocal lens optical system are eccentric and direct light rays from the same image onto the macula of an eye.

Another advantage of the present system is that the imaging producing means can be so arranged that when one lens system is in use, the light allowed to go through the other or unused lens system is minimized or completely eliminated. By placing the "near optical vision system" superiorly on the artificial lens, the upper eyelid position can be varied and thereby be utilized to cover up the nearest system while primarily using the "distant optical vision system" to pass selected paracentral light rays from an image onto the macula.

Another advantage of the present invention is that the pupil size can be altered or reconfigured by making the pupil larger and preferably an elongated vertically shaped elliptical natural pupil. By altering the pupil size or configuration, the quantity of available light is increased to 150% to 175% of the light that would have traversed the untreated or unaltered pupil. This is a marked improvement over the prior art lens system where the transmitted light is divided between the two lens system. Therefore, approximately 65% to 75%, light (compared to the quantity of the light passing through the pupil before treatment) would be available for the lens system of the present invention to use to focus light rays from the images on the macula. If the pupil is not altered, only approximately 40% of the light is available for each optical system. This is typical of the numerous lens design of the prior art described above.

Another advantage of the present invention is that the artificial lens of the present invention can have one or both of the imaging lens system configured with an extended objective lens to function as a light gathering means.

Another advantage of the present invention is that eccentric location of the near system in a superior position can be utilized in an unaltered pupil.

Another advantage of the present invention is that further eccentricity of the near lens system is achievable by altering the natural pupil by vertical elongation of the natural pupil or by use of an accessory pupil.

BRIEF DESCRIPTION OF THE DRAWINGS

These and other advantages of this invention will be readily apparent when considered in light of the detailed description hereinafter of the preferred embodiment and when considered in light of the drawings set forth herein which include the following figures:

FIG. 5 is a pictorial representation of an artificial lens of the present invention formed as an intraocular lens located in the anterior chamber of an eye;

FIG. 6 is a pictorial representation of an artificial lens of the present invention formed as an intraocular lens located in the posterior chamber of an eye;

FIG. 7 is a pictorial representation of an artificial lens of the present invention affixed to the cornea of an eye subepithelially;

FIG. 8 is a pictorial representation of an artificial lens of the present invention which is implanted as an intracorneal lens intrastromal;

FIG. 9 is a pictorial representation of an artificial lens of the present invention having a near lens system superior and a distant lens system inferiorly, in an eccentric arrangement, with the position of both lens system being below the upper eyelid;

FIG. 10 is a pictorial representation of the position of the image producing means of FIG. 9 observing images below the eyelid;

FIG. 11 is a pictorial representation of an eye having an artificial lens of the present invention wherein the image producing means includes a first lens system and a second lens system wherein the near lens system is covered by the upper eyelid resulting in only the second lens system passing light rays from a distant object to the macula of the eye;

FIG. 12 is a pictorial representation of an eye having image producing means wherein the near lens system is occluded by the upper eyelid resulting in only the light rays from the distant object being passed by an artificial lens of this invention to the macula of an eye;

FIG. 20 is a pictorial representation of an artificial lens of the present invention having an extended objective lens and a prism in the superior location in an altered elongated natural pupil and a plano-convex lens and a prism in the normal natural pupil;

FIG. 21 is a front plan view of the artificial lens of FIG. 20;

FIG. 22a is a pictorial representation of an artificial lens system having an extended objective lens in accessory pupil;

FIG. 22b is a pictorial representation of an artificial lens having an extended objective lens in both the accessory pupil and natural pupil with a third extended objective lens alternative;

FIG. 22c is a pictorial representation of an artificial lens having an extended objective lens in the natural pupil;

FIG. 23 is a front plan view of an artificial lens in the form of an intraocular lens having an extended objective lens and a prism in the superior location on the lens and an extended objective lens located inferior on the lens;

FIG. 24 is an elevational end view of the intraocular lens of FIG. 23;

FIG. 25 is a pictorial representation of the eye showing the natural pupil and an accessory pupil having the intraocular lens of FIG. 23 implanted in the eye;

FIG. 26 is a pictorial representation of the eye showing the natural pupil being formed into a vertically extending ellipitical shape forming an enlarged pupil which is in lieu of an accessory pupil and having the intraocular lens of FIG. 23 implanted in the eye;

FIG. 27 is another embodiment of an artificial lens in the form of an intraocular lens having a lens with an extended objective lens and a prism located superiorly on the lens and a plano-convex lens in the natural pupil;

FIG. 28 is a pictorial representation of an eye having a natural pupil which is formed into an enlarged pupil with the intraocular lens of FIG. 27 implanted therein and showing the various positions of the upper eyelid to control passing of light rays from a near image through the extended objective lens;

FIG. 29a shows a pictorial representation of the eye having a natural lens and an intrastromal lens having a plano-convex lens and a "base up" prism located superiorly within the cornea of an eye to form an image through the natural pupil;

FIG. 29b is a pictorial representation of a near lens system having a "base up" prism;

FIG. 29c is a pictorial representation of a near lens system having a "base down" prism; and FIG. 30 is a pictorial representation of an eye having a partial (no superior cut) radial keratotomy and a vertically elongated natural pupil for receiving light rays from an intracorneal lens located superiorly in the stroma in front of the pupil for passing a separate image through the enlarged natural pupil.

DESCRIPTION OF THE PREFERRED EMBODIMENT

Figures 1A, 1B, 1C:
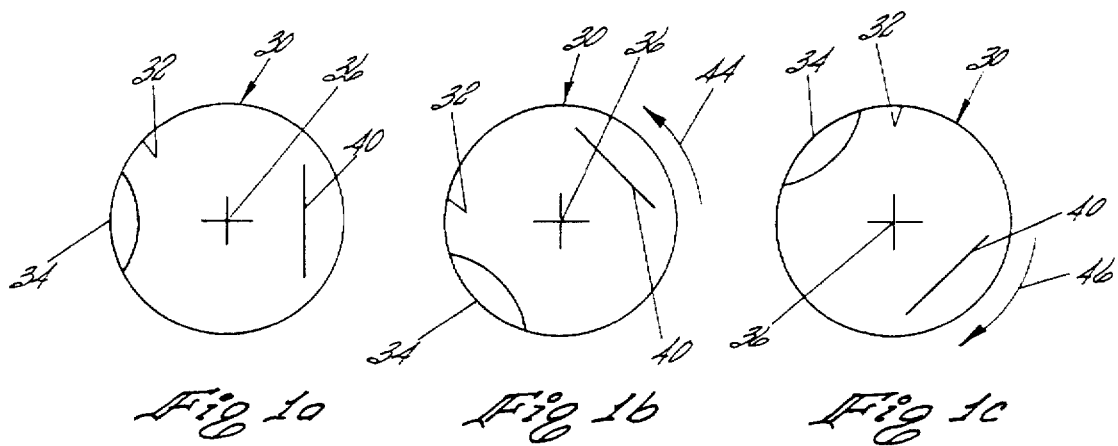
FIG. 1a is a pictorial representation of the eye illustrating a first rotation position of the eye about its rotational axis with the pupil looking straight ahead showing the positional relationship between the natural crystalline lens and the macula.
FIG. 1b is a pictorial representation of the eye illustrating a second rotation position of the eye about its rotational axis with the pupil looking upward showing the positional relationship between the natural crystalline lens and the macula.
FIG. 1c is a pictorial representation of the eye illustrating a third rotation position of the eye about its rotational axis with the pupil looking downward showing the positional relationship between the natural crystalline lens and the macula.

Before beginning with the description of the preferred embodiment, the following background information is provided for a better understanding of the present invention.

The anatomical center of the human eye is not necessarily the optical center of the human eye. The anatomical center of the human eye is calculated or derived from measurement of the diameter of the cornea, and this dimension can be obtained by using techniques well known in the art. However, the optical center of the human eye is generally slightly nasal and downward relative to the anatomical center.

The angular difference between the optical center and the anatomical center is generally known in the art as the angle kappa (κ). For example, the optical center may be 3° and 1.5° inferior to the anatomical center. It is known in the art that the above angular differences could be as much as about 6° to about 7° or more.

In addition, the term "fovea centralis" refers to the small, rodless depression of the retina in line with the visual axis which affords acute vision. The term "fovea vision" refers to vision being accomplished by looking directly at objects in daylight so that the image falls on or near the fovea centralis. This is also known as photopic vision. The term "macula" refers to the anatomical structure of the eye having the form of a spot as differentiated from surrounding tissue.

The fovea centralis is located in the macula of the eye, which, in turn, is a component of the retina of the eye. Sometimes the fovea centralis is the area referred to as the macula upon which the image is actually focused. A location referred to herein as superior of the macula describes a location position situated generally above the macula while a location referred to herein as "inferior" to the macula describes a location position situated generally below the macula.

The term "accommodation" describes the following characteristics of the eye. When the brain perceives that attention of the person is required for near, enervation is initiated to the ciliary body, which is a circular, sphincter type, muscle located just behind the iris for 360 degrees; by means of the occulomoter nerve. The muscle contracts and in so doing brings about relative relaxation of the zonules. Slackened zonules result in decreased lateral traction on the capsule of the crystalline lens. As a result, the elastic quality of the capsule causes the lens to seek the shape of greatest volume which is that which is most spherical. This in turn results in an increase in the anterior-posterior diameter of the lens. This results in an increase in plus dioptic power of the lens. As a consequence, the focal point of the optical system of the eye moves anteriorly, that is closer to the front of the eyes. Divergent rays from an object at near which would have come into focus behind the retina are thereby brought to focus on the macula of the retina.

The term "eccentric" means situated to one side with reference to a center as contrasted to the word concentric which pertains to the relationship between two different sized circular, cylindrical or spherical shapes when the smaller one is exactly (or substantially) centered with the larger one.

Referring now to FIGS. 1a, 1b and 1c, the human eye is shown generally as 30 with the retina being shown generally as 32. The macula including the fovea centralis is shown generally as 34. The pupil 40 is spaced a predetermined distance from the macula 34. As illustrated in FIG. 1a, the lens has a central rotational axis 36 about which the eyeball rotates.

FIG. 1a shows the eye of the human wherein the eyeball is positioned such that the pupil looks straight ahead to an object. The image of an object observed by the eye passes through the pupil 40 onto the macula 34.

FIG. 1b illustrates how the eyeball rotates when a person looks upward in the direction as shown by arrow 44. The pupil 40 moves upward in the same direction as the arrow 44 while the macula 34 moves in an opposite direction. Thus, the image of an object is passed through the pupil 40 and is directed onto the macula 34.

In a similar manner, FIG. 1c shows the rotation of the eye when a person looks downward as illustrated by arrow 46. The image perceived by the user from an object passes through the pupil 40 and onto the macula 34.

Figures 2, 3:
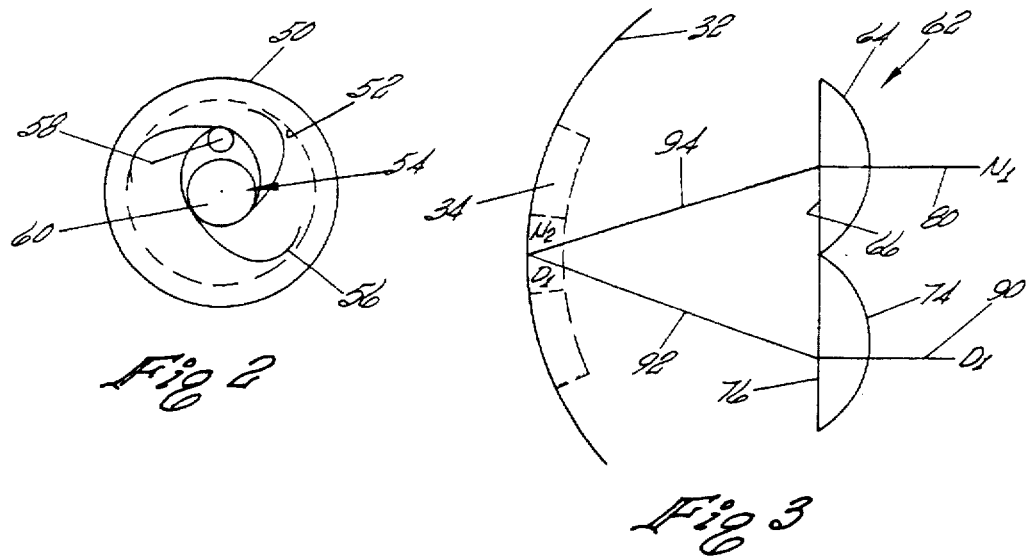
FIG. 2 is a front view of an eye having an artificial lens in the form of an intraocular lens having an eccentric lens system for producing near and distant macular images.
FIG. 3 is a pictorial representation of an image producing means comprising a first lens having a predetermined diopter power and a second lens having a preselected diopter power eccentric to the first lens for focusing similar images onto the macula in an eye.

FIG. 2 illustrates pictorially an eye 50 having a posterior capsule shown by dashed line 52. An artificial lens of the present invention, shown generally as 54, is in the form of an intraocular lens having a near lens system 58 located superiorly of a distant lens system 60 supported in the eye by three haptics 56. The artificial lens 54 is adapted for use in the human eye. The artificial lens 54 is a multifocal optical lens system wherein the principal axis of each lens is eccentric to each other for directing light rays from each image lens of the multifocal optical lens system onto a macula of an eye. In the preferred embodiment as illustrated FIG. 2, the artificial lens 54 includes a near lens vision system 58 and a distant lens vision system. In this embodiment, the multifocal optical lens system includes a first lens system which is adapted for receiving light rays from a near object and a second lens system which is adapted for receiving light rays from a distant object. The principal axis of each lens is eccentric to each other.

FIG. 3 shows one embodiment of the present invention wherein the artificial lens 62 is adapted for producing similar images from the same object from lens in an eccentric arrangement wherein light rays from each object are directed upon the macula 34. In FIG. 3, the first lens system includes a first lens 64 having a predetermined diopter power for receiving light rays from a near object shown as $N_1$ and the light rays illustrated by line 94 are directed onto the macula. The first lens 64 has a selected surface 66 located on the anterior surface thereof.

In the embodiment illustrated in FIG. 3, a second lens system includes a second lens 74 having a second selected surface 76. The second lens 74 is in a form of a planoconvex lens adapted to pass light rays from a distant object shown as $D_1$ and for directing the light rays 92 from a distant object onto the macula 34 of the eye. The two lens systems have an eccentric relationship.

Thus, light rays $N_1$ from a near object passes along a path shown by line 94 through the first lens 64 and is directed to the macula 34 shown as $N_1$.

In the second lens system, light rays from the distant object shown as $D_1$ are passed along a path shown by line 92 through the selected surface 76 of the lens 74 and then is directed along a path shown by line 92 to the macula of the eye 34 as shown by $D_1$.

Figure 4:
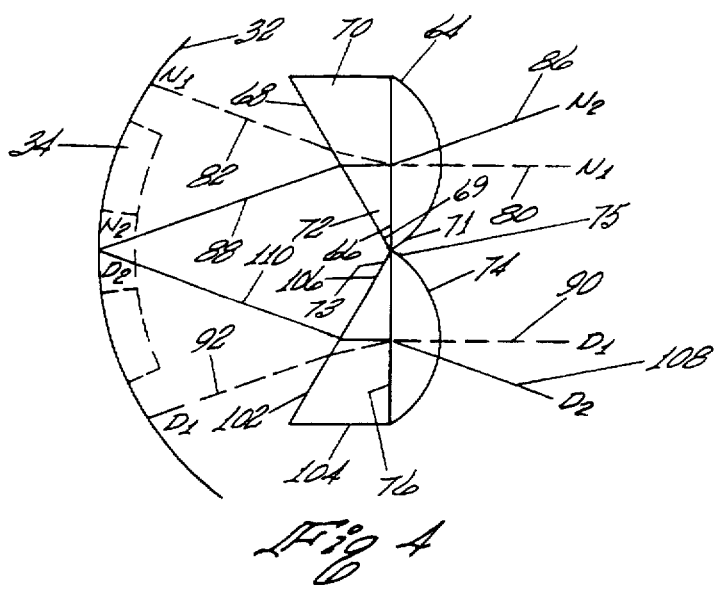
FIG. 4 is a pictorial representation of an image producing means having a first lens having a prism and a second lens having a prism for directing light rays from near and far objects onto the eye, with the near image $N_1$ directed superior to the macula and the distant image $D_1$ inferior of the macula.

FIG. 4 is an alternative embodiment of the artificial lens 62 adapted for use in the present invention. In FIG. 4, the first lens 64 includes a prism 68 having a preselected diopter power which is positioned with its base 70 in a "base up" position such that the wedge-shaped edge 66 is positioned adjacent the edge of the second lens 74. Referring to FIG. 4, the first lens 64 has a first prism 68 mounted on a surface of the first lens 64. The first prism 68 is wedge-shaped and has a wedge-shaped edge 69 which is situated adjacent the proximal edge 71 of the first lens 64. The second lens 74 has a second prism 102 mounted on a surface of the second lens 74. The second prism 102 is also wedge-shaped and has a wedge-shaped edge 73 which is situated adjacent the proximal edge 75 of the second lens 74. As shown in FIG. 4, the wedge-shaped edges 69, 73 of the first and second prisms 68, 102 are located adjacent each other and in proximity to the proximal edges 71, 75 of the first and second lenses 64, 74. As illustrated in FIG. 4, the prism 68 is positioned against the selected surface 66 of the first lens 64 of the first lens system.

In the second lens system, the second lens 74 includes a second prism 102 having a preselected diopter power which is positioned with the base 104 in a "base down" position such that wedge-shaped edge 106 is positioned adjacent the edge 72 of the prism 68 affixed to the selected surface 66 of the first lens 64.

The light rays from the near objects are passed by the first lens 64 and prism 68 and light rays $N_1$ and $N_2$ from the near objects transverse the paths shown by dashed line 80 for $N_1$ and solid line 86 for $N_2$. The light rays shown by dashed line 80 pass through the first lens 64 and are directed by prism 68, by deflection towards the base 70, to a location superior of the macula shown by dashed line 82.

However, the path traversed by the light rays from the distant objects are different. As illustrated in FIG. 4, the light rays from the distant objects shown as $D_1$ pass along a path shown by dashed line 90 through the second lens 74 and through the prism 102 wherein the prism 102 directs the light rays from the distant object along a path shown by dashed line 92 to a location inferior of the macula 34 as shown by $D_1$. The light rays $D_2$ from the distant object are passed along a path shown by solid line 108, through the second lens 74 and, through the prism 102 where the image is deflected towards the base 104. The prism 102 directs the light rays from the distant image along the path shown by solid line 110 to the macula as shown by $D_2$.

FIG. 4 shows that by utilizing the two prisms 68 and 102, the prisms function to separate the light rays from different objects into separate light ray paths wherein the light rays of some of the objects, the paracentral light rays, are directed onto the macula and the remainder of the light rays, the central light rays, of some of the objects are directed to a location at least one of superior to the macula for near and inferior to the macula for distant objects. Thus, paracentral rays are directed to the macula from distant and near objects.

FIG. 5 illustrates the implantation of an artificial lens in the form of an intraocular lens shown generally as 132 into an eye shown generally as 116. The intraocular lens 132 is located in the anterior chamber of eye 116 and is spaced from the cornea 118. The iris 120 and ciliary processes 124 define the irdiocapsular cleft 122 which is located in the posterior chamber of the eye 116. The hyaloid membrane 126 has an end 130 which is attached to the ciliary processes 64. The hyaloid membrane 126 maintains the vitreous humor 128 within the eye.

As illustrated in FIG. 5, an artificial lens of the present invention in the form of intraocular lens 132 has a near lens system 136 and distant lens system 138. Resilient support members shown generally as 140, which may be four equally spaced haptic members, and its associated annular-shaped guide and support elements are located forward of the pupil 120. The resilient support members 140 and their associated annular-shaped guide and support elements support the intraocular lens 132 having the first lens system and the second lens system formed therein in the anterior chamber of the eye 116.

FIG. 6 illustrates an alternate location of the intraocular lens in the eye 116. In FIG. 6, an artificial lens 132 utilizing the teachings of this invention is implanted in the posterior chamber of the eye 116. Typically, the resilience support means 140 and their associated annular-shaped guides and support elements which formed part of the intraocular lens 132 are located within the capsular bag shown by dashed lines 150 of the original natural crystalline lens.

The intraocular lens utilizing the artificial lens of the present invention could be located with the resilient support means 140 of the lens 132 being positioned in the ciliary sulcus which is located between the iris 120 and the ciliary processes 124 or in the capsular bag 150 of the natural crystalline lens after the natural crystalline lens is removed by using known surgical procedures. The resilient support means 140 of lens 132 can comprise two to four haptic members which are equally spaced around the outer peripheral surface and the plane substantially coplaner, or with 5° to 10° angulation which is deemed to be substantially coplanar, with the lens body. In the alternative, the resilient support beams could comprise three haptic members (similar to FIG. 2) or more, such as four haptic members (FIG. 5) equally spaced thereon the outer peripheral surface of the lens body and in a plane substantially coplaner, or with 5° to 10° angulation which is deemed to be substantially coplanar, with the lens body. The reference to a resilient support means 140 as illustrated FIGS. 5 and 6 includes a two haptic member, three haptic member or four haptic member resilient support.

FIG. 7 illustrates another embodiment of an artificial lens which utilizes the teachings of the present invention in the form of a corneal overlay lens which is adapted to be affixed to the surface of the cornea 118 of eye 116 subepithelially. The artificial lens shown generally as 142 includes a near lens system 144 and a distant lens system 148. The artificial lens 142 is positioned centrally within a lens body 152.

It is envisioned that the corneal lens body 152 forming the artificial lens 142 can be implanted using known surgical techniques for affixing an artificial lens to the cornea of an eye with a patient's epithelium covering the anterior surface of the lens.

FIG. 8 is another embodiment of an artificial lens of the present invention in the form of an intracorneal lens shown as artificial lens 142. Artificial lens 142 has a near lens system 144 and the far lens system 148 with an eccentric relationship. The artificial lens 142 is implanted within the stroma, or intrastromally, of the cornea 118 using known surgical implantation techniques. The structure of the artificial lens 142 is the same as that illustrated on FIG. 7. In the case of myopia, a concave (negative) lens could be used for distance in place of lens system 148 and if necessary for near in place of lens system 144.

A similar arrangement for eccentrically arranged lens without prism, similar to FIG. 3, can be used in a similar lens.

FIGS. 9, 10, 11 and 12 illustrates the lens of FIG. 2 positioned within an eye 156 having an upper eyelid 158 wherein the eyelid has the edge thereof defined by dashed line 160. The artificial lens 50 is positioned on the eye as described herein before and when the user directs the eye to look generally downward in a direction as shown in FIG. 10, the near vision system 58 and the distant vision system 60 are both positioned below the edge 160 of eyelid 158. However, the distant vision system is blocked by the lower eyelid 162 by edge 164 shown by dashed line being interrupted by the lower eyelid 162, and the near system is the only system positioned to receive light.

FIG. 10 shows the relationship between the eye 156, the eyelid 158 including edge 160 thereof and the artificial lens 54 thereof supporting the near vision system 58 and the far vision system 60 in a position below the eyelid edge 160.

FIGS. 11 and 12 depict the same relationship except that the eyeball has been adjusted into a position similar to that depicted by FIG. 1b hereinabove or the upper eyelid has been lowered. In that position, the near image system 58 is moved past the eyelid edge 160 and under the eyelid 158. Thus, the distant vision system 60 is the only portion of the image producing means which is adapted to receive light.

FIG. 12 illustrates the relationship between the artificial lens 50 and edge 160 of the eyelid 150. The near vision is blocked. This illustrated by the dashed line being interrupted by the upper eyelid 158.

This selective coverage of the near lens system is possible because of the eccentric arrangement of the lens system.

In FIG. 10, the user receives light rays from both a near image and a distant object, and selected paracentral light rays are directed onto the macula as described hereinbefore. In FIG. 12, only light rays from the distant vision system are received by the macula through the distant vision system 60.

Figure 13:
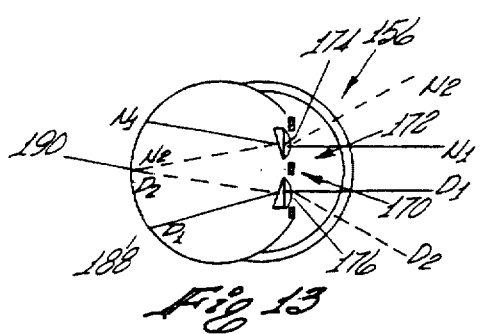
FIG. 13 is a pictorial representation of a pupil having an accessory pupil formed therein wherein a first lens system is located posteriorly to the accessory pupil and the second lens system is located posteriorly to the natural pupil.

FIG. 13 discloses another embodiment of the present invention wherein the artificial lens is posterior to and is adapted to cooperate with a pupil 170 of eye 156 which has been altered and reconfigured. In FIG. 13, the iris has been altered to form an auxiliary pupil 178 located superiorly.

Figure 14:
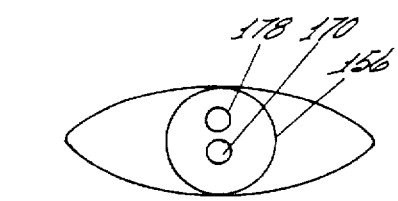
FIG. 14 is a pictorial representation of an eye showing the front view of the eye having an accessory pupil formed therein for cooperating with the first lens system and wherein the natural pupil cooperates with the second lens system.

There are two ways for accomplishing the alteration and reconfiguration of the iris. FIG. 14 illustrates one method wherein an accessory pupil 178 is formed in a location superior to the natural pupil 170. Thus, the iris would have two distinct pupils, a natural pupil 170 and an accessory pupil 178. This has the advantage of cooperating with the separation or eccentricity between the principal axes of the near lens system and distant lens system, implanted or affixed to the eye even greater. Also, there is no diffraction of the light of the interface between the two lens systems.

Figure 15:
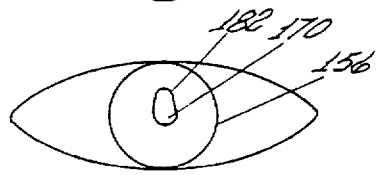
FIG. 15 is a pictorial representation of an eye having an altered pupil to form the same into a vertical ellipitically shaped pupil for cooperating with an image producing means having a first lens system and a second lens system eccentrically arranged.

FIG. 15 shows another method for altering and reconfiguring the pupil 170 to make the same larger. As illustrated FIG. 15, the equivalent to an accessory pupil, area 182, is formed by enlarging the natural pupil 170 to make the same into an elongated vertically elliptical shape pupil.

Referring again to FIG. 13, the artificial lens 172 would then be positioned with the near imaging system 174 located in the accessory pupil 178 and the distant imaging portion 176 would be located in the natural pupil 170.

By altering the size of pupil 170 and reconfiguring the same or by making an accessory pupil, the quantity of available light is increased to about 150% to about 175% of the light that would have been passed by the untreated or unaltered pupil 170. The altered pupil is adapted to cooperate with a first lens system and a second lens system eccentrically arranged. This represents a significant improvement with respect to the transmitted light being divided equally between the near image system 174 and the distant image system 176. The path of the light rays are shown generally by dashed lines 186 for the near vision and dashed line 188 for the distant vision. Again, the disparate images are directed onto macula 190 of eye 156.

Typically, the diameter of a lens to be located in the accessory pupil or the enlarged portion of an elongated vertically elliptically shaped pupil would be in the order of 2.0 mm to 4 mm.

Figure 16:
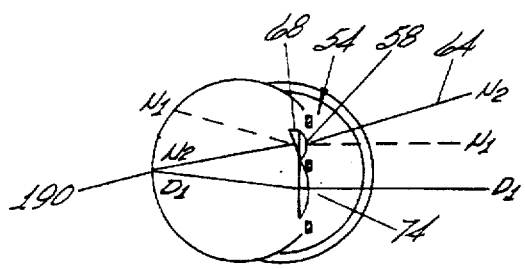
FIG. 16 is a pictorial representation of an image producing means having a first lens system having a first lens and a prism and a second lens system having a second lens located in the accessory pupil and natural pupil, respectively.

FIG. 16 depicts that the artificial lens system 54 of FIG. 3 could likewise be used in the eye having the altered and reconfigured principal as illustrated in FIG. 16. In FIG. 16, the macula 190 would receive light ray $N_2$ from near objects and light ray $D_1$ from far objects. Since the near lens 58 has a prism 68, prism 68 directs light rays from a near object onto a location superior to the macula 190 as illustrated by $N_1$ in FIG. 16. Light rays $N_2$ from a different near object would be transmitted to the macula.

Figure 17A:
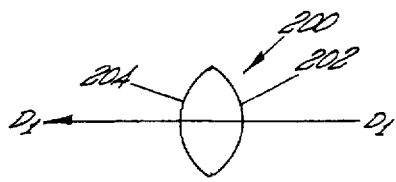
FIG. 17a is a pictorial representation of a bi-convex lens.
Figure 17B:
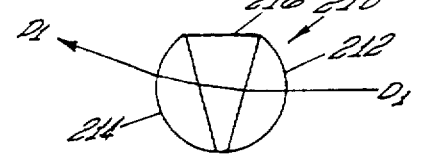
FIG. 17b is a pictorial representation of a double convex lens having a prism operatively connected there between adapted for use as a lens system.
Figure 17C:
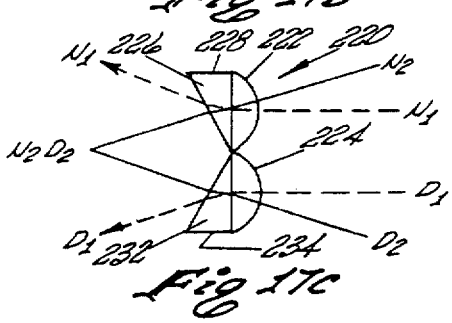
FIG. 17c is a pictorial representation of a first lens system having a prism and a second lens system having a prism.

FIG. 17a, FIG. 17b and FIG. 17c depict different embodiments of lens systems adapted for use in either the near or distant lens system in an artificial lens for practicing this invention. FIG. 17a depicts a lens structure for either one of the near vision system or distant vision system. The image producing means is depicted by lens system 200 having a bi-convex lens formed by a pair of plano-convex lens 202 and 204. Similarly a plano-convex lens could be used. In FIG. 17a, the bi-convex lens formed by lens 202 and 204 are joined or fused together forming a homogenous lens. In this embodiment, light rays $D_1$ from a distant object would pass through the lens system and be directed onto the macula. Thus, light rays from similar macular images of the same object would be developed by two eccentric, independent bi-convex lens system or plano-convex lens system.

FIG. 17b shows another embodiment of an artificial lens image system of the present invention showing that one of the imaging lens could be in the form of a bi-convex lens 210 having a first plano-convex lens 212, a second plano-convex lens 214 and a prism 216 positioned therebetween. In practice, these lens would fused to make a homogenous lens. By controlling the ratio of the length of the base to the angle of the edge of the prism, the angle of incidence of the light ratio shown by $D_1$ can be controlled to direct the light rays from a near object onto the macula or to a position superior to the macula. A second lens system in the form of that of FIG. 17b could be reversed placing the base of the prism 216 in a position opposite to that illustrated in FIG. 17b to cause one of the images to be formed at a location inferior to the macula whether involving the near vision system or the distant vision system.

FIG. 17c shows another embodiment of the lens system illustrated in FIG. 4 and the lens body has been modified using prisms having a larger base. The artificial lens system 220 includes a first plano-convex lens 222 and a second plano-convex lens 224. Plano-convex lens 222 has a prism lens 226 incorporated in the back or posterior surface thereof wherein the length of the base 228 is selected to control the angle of incidence such that the light rays from a near object is directed at sufficiently superior of the macula to avoid placing similar blurred images on the macula. Light rays $N_2$ from a different object would be projected on the macula resulting in disparate macula images.

In a similar manner, plano-convex lens 224 has a prism lens 232 affixed to the posterior surface thereof wherein the base 234 of the prism 232 being positioned in an opposed relationship to that of the base 228 affixed to the first plano-convex lens 222. Again, the length of the base 234 of prism 232 is selected to be of a length to cause light rays $D_1$ from a far object to be directed at a predetermined location inferior of the macula to avoid placing a similar blurred distant image onto the macula. Light rays $D_2$ from a different object would be projected on the macula resulting in disparate macula image from the near vision system and the distant vision system.

Figure 18:
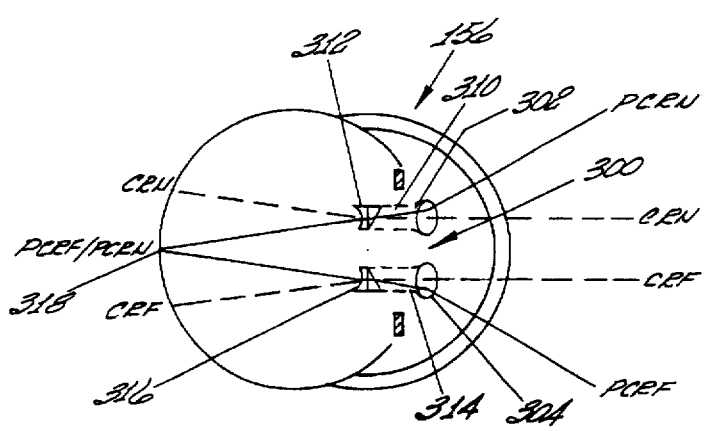
FIG. 18 is a pictorial representation of an image producing means having a pair of extended objective lens having a lens system including a prism located at the distal end thereof for producing disparate macular images.
Figure 19:
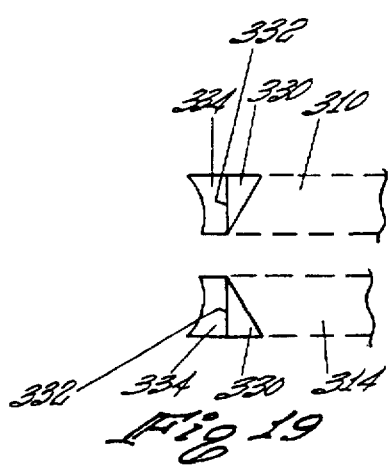
FIG. 19 is a pictorial representation of the distal section of the lens system illustrated in FIG. 18 showing another embodiment of an image producing means.

FIGS. 18 and 19 illustrate an alternative of an artificial lens for practicing the invention wherein the imaging producing means defines a first lens system and second lens system which each include an extended objective lens to increase the amount of light collection by the artificial lens and passed to the posterior segment of the eye. FIG. 18 illustrates that the eye 156 has the artificial lens system shown generally as 300 extending through iris opening into the anterior chamber thereof. The artificial lens system 300 includes a first extended objective lens 302 and a second extended objective lens 304. The objective lens 302 extend into the anterior chamber of the eye 156. As shown by FIG. 18, the distant end of each objective lens 302 and 304 terminates in a surface as illustrated at the distal lens 310 of extended objective lens 302 and distant lens 314 of the extended objective lens 304. The distal lens 310 includes a shaped lens/prism member 312 with the base of the prism in a "base up" position. The distant end of the distant extended objective lens 304 has a shaped lens/prism member 316 with the base of the prism being located in a "base down" position. Although, for purposes of this disclosure, the lens are described as separate and opposed; in practical application, the lens are fused together and homogenous. The effect of the prism is to change the angle of the ocular lens (posterior lens) in relationship to the longitudinal axis of the lens system. The prisms are positioned in an opposed spaced relationship to each other.

In the event that the length of the extended objective lens is of a length which extends through the posterior capsule, a procedure referred to as capsulorhexis can be performed on the posterior capsule to form opening in the posterior capsule. In such event, the posterior end of the lens system would extend into the vitreous humor.

FIG. 18 illustrates that the paracentral ray near ("PCRN") passes through the objective lens 302, the midsection 310, the shaped lens/prism member 312 and the PCRN is focused onto the macula 318. In a similar manner, the central ray near ("CRN") passes through the extended objective lens 302 to the distal end 310 where the image is deflected by the prism to position the CRN superior of the macula 318.

The far extended objective lens 304 receives the paracentral ray far ("PCRF") and passes the same through the midsection 314 where the prism 320 then directs the PCRF ray through shaped lens/prism member 316 onto the macula 318.

Similarly, the extended objective lens 304 receives the central ray far ("CRF") and passes the same to the midsection 314 where the prism directs the CRF to a location inferior of the macula 318.

FIG. 19 shows another embodiment of the extended objective lens system of FIG. 19 wherein the midsections 310 and 314 are terminated by a different lens system. Specifically, midsection 310 of the extended objective lens 302 and midsection 314 of the extended objective lens 304 are each terminated posteriorly in a prism 330 at the respective midsections 310 and 314. The bases of the prisms 330 are positioned in a "base up"/"base down" relationship as shown in FIG. 19. The prisms each have a posterior surface 332 for supporting a negative lens 332.

The light rays pass through the midsection 310 and are deflected by the prism 330 through the negative lens 334 such that the light ray CRN is directed superior of the macula and the light ray PCRN is directed onto the macula. By allowing an extension of the lens systems from the posterior chamber into the anterior chamber as illustrated in FIG. 18, the following advantages are obtained. The CRF and PCRF light rays passing through the extended objective lens 304 are directed such that the PCRF light rays go to the macula and the CRF light rays inferior to the macula.

The lens system 300 provides a greater collection of possible light. Due to the objective lens in the extension, there is an increase in the field of vision. Further, by utilizing the extended objective lens, there is a decrease in the problems of centering the lens.

The combination of a plus power objective lens in the anterior chamber and a minus power ocular lens in the posterior chamber or vitreous constitutes a totally intraocular galelian telescope. The purpose of this light gathering and magnification (enlargement) of the image is for use in patients with macular degeneration.

By utilizing different lens structure in FIGS. 18 and 19, it is possible that specific lens structures could be developed for special applications for macular degeneration wherein the retinal image can be spread over more of the retina to stimulate more of the sending neurons to the brain thereby improving the ability of the brain to interpret the image.

By utilizing extended objective lens, the overall size of the artificial lens base could be made smaller resulting in smaller incisions needed for insertion.

In FIG. 20, the artificial lens 340 in the form of an intraocular lens is implanted in an altered pupil within the eye 156. The artificial lens 340 includes an extended objective lens 342 and a "base up" prism 344 which are adapted to be located to be in the superior location of the enlarged pupil, such as superior in the enlarged vertically extending ellipitical shaped area of the natural pupil 170 as illustrated in FIG. 15 which is functionally equivalent to the accessory pupil. The artificial lens 340 also includes a plano-convex lens 348 and a "base down" prism 350 which are adapted to be located in the natural pupil 170. A similar lens system without prisms for similar macular image is a variation of this novel concept.

The artificial lens 340 illustrated in FIG. 20, the PCRN passes through the extended objective lens 342 and is deflected by the "base up" prism onto the macula and the CRN is directed to a location superior of the macula. In this structure, the objective lens collects more light for near vision due to its extension into the anterior chamber. The optical surface of the objective lens can be made larger to create a larger field of vision.

In the lower section of the artificial lens, the PCRF rays pass through the plano-convex lens 348 and are directed by the "base down" prism 350 onto the macula. The CRF rays are passed through the plano-convex lens 348 and are deflected by the "base down" prism 350 inferior of the macula and the PCRF is directed onto the macula.

FIG. 21 illustrates in a front plan view artificial lens 340 of FIG. 20. The extended objective lens 342 is positioned on the plano-convex lens 348 in a superior position on lens 348 (eccentrically arranged). The "base up" prism is located on the reverse surface of lens 342. The central body lens 348 likewise has its prism 350 located "base down" on the reverse surface. The artificial lens 340 includes three haptic members 352 spaced substantially equal to hold the intraocular lens in the eye as described hereinbelow.

In the pictorial representation of FIGS. 22a, 22b and 22c, various other possible configurations for intraocular lens utilizing the teaching of this invention are shown. FIG. 22a illustrates an artificial lens system implanted in an eye 156 wherein the artificial lens has an extended objective lens 360 which is adapted to be located in the accessory pupil 178 and any other suitable lens may be used in the natural pupil 170. This arrangement can utilize prisms for disparate macular images and without prisms for similar macular images.

FIG. 22b illustrates an artificial lens system implanted in an eye 156 wherein the artificial lens has extended objective lens 360 and 370 wherein objective lens 360 is adapted to be located in the accessory pupil and extended objective lens 370 is adapted to be located in the natural pupil 170. In addition, for a trifocal lens equivalent, a third extended objective lens 372 can be located within the natural pupil 170.

The concept of a trifocal structure illustrated in FIG. 22b is exemplary, and any artificial lens of the invention can utilize the trifocal concept.

FIG. 22c illustrates an artificial lens system implanted in an eye 156 wherein the artificial lens has an extended objective lens 370 which is adapted to be located in the natural pupil 170 and any other suitable less may be used in the accessory pupil 178. These are all variations of eccentric lens systems.

FIGS. 23 and 24 illustrate an artificial lens in the form of an intraocular lens 378 having an extended objective lens 374 having a plano-convex lens on the surface and a "base up" prism 382 in the superior location of the lens and an larger extended objective lens 376 having a plano-convex lens on the surface located in the inferior location on the lens 378. The diameter of lens 374 could be in the order of about 2.5 millimeters and the diameter of lens 376 could be in the order of about 3.0 millimeters.

The structure of the intraocular lens in FIGS. 23 and 24 permit an additional quantity of light rays to be is directed onto the macula which counteracts the decreased amount of light available by using two lens systems.

FIG. 25 is a pictorial representation of the eye showing the natural pupil 170 and an accessory pupil 178 having the intraocular lens 378 of FIG. 23 implanted in the eye. The intraocular lens 378 of FIG. 23 is implanted in the eye with lens 374 being located posterior to the accessory pupil 178 and lens 376 located posterior to the natural pupil 170. Again, a prism is used for disparate macular images and no prism for similar images.

FIG. 26 is a pictorial representation of the eye showing the natural pupil 170 being formed into a vertically extending ellipitically shaped pupil forming an enlarged area 170' which is in FIG. 25. The intraocular lens 378 of FIG. 23 represented by dashed lines is implanted in the eye with lens 374 being located in the enlarged pupil 170' and lens 376 located in the natural pupil 170.

Referring now to FIG. 27, the embodiment of an intraocular lens of FIG. 27 is in the form of plano-convex lens 388 having with an extended objective lens 392 and a "base up" prism 394 located superiorly on the lens. A plano-convex lens 390 is used for a distant image. This embodiment produces separate light rays from another object which is directed onto the macula 34 (disparate macular image). Similarly, the lens system arrangement can be used without prisms for similar macular images.

FIG. 28 is a pictorial representation of an eye having a natural pupil 170 which is formed into an enlarged pupil 178 having a vertically extending ellipitical shape with the intraocular lens of FIG. 27 implanted therein. FIG. 28 also shows the various positions of the upper eyelid shown in the open position represented by dashed line 160 to pass an image through the extended objective lens 392. The upper eyelid is also shown in the blocking position as represented by dashed line 162 wherein light rays from a near image is a blocked from passing through the extended objective lens 392. The distant image is passed by lens 390. A similar effect would be obtained with an accessory pupil used with the lens system with or without a prism.

FIG. 29a shows a pictorial representation of the eye having a natural lens 400 in the eye. An intracorneal lens having a plano-convex lens 402 is located superiorly within the cornea of the eye to pass light rays from an object through the superior part of the natural lens 400 and directs the paracentral light rays from the near object onto the macula 34. The intracorneal lens having the plano-convex lens 402 is eccentric to the natural lens 400.

FIGS. 29b and 29c show pictorially alternative arrangements of the plano-convex lens 402 having a prism 404 or 404'. In FIG. 29b, the prism 404 is mounted "base up" and in FIG. 29c, the prism 404' is mounted "base down".

In all of these instances, the lens of FIGS. 29a, 29b, and 29c are all arranged eccentrically to the natural lens 400.

FIG. 30 is a pictorial representation of an eye having a partial (no superior cut) radial keratotomy having formed in the cornea thereof seven (7) elongated angularly disposed slits or cuts 406 spaced over less than 360° of the eye (approximately 318° as shown in FIG. 30) leaving the superior location of the eye untreated with elongated slits or cuts. This untreated area of the cornea of the eye then has the natural pupil enlarged to from a vertically extending elongated ellipitically shaped pupil. Near lens 402 with or without prisms 404 and 404' is implanted in the enlarged area pupil area for passing a light ray from a near object through the accessory pupil to the macula.

These principles apply also to a four (4) cut radial keratotomy with oblique cuts (at 1:30; 4:30; 7:30 and 10:30 positions having no superior cuts).

One of the important teachings of the present invention is that the size and/or shape of a natural pupil can be altered to accommodate means adapted to be affixed to an eye having multifocal lens system wherein the principal axes are eccentric, such as for example, by implantation, intracorneal insertion or corneal overlay.

It is envisioned that the natural pupil can be altered using known techniques such as for example, Yag laser, Argon laser or other known surgical techniques.

A Yag laser is typically used for cutting and care must be taken to insure that the Yag laser does not hit, damage or perforate the natural crystalline lens.

An Argon laser is essentially a coagulation device. It is known that the Argon laser, when directed to the iris distorts the pupil. This is generally referred to as "puckering".

Other surgical techniques includes performing a sector iridectomy which forms a keyhole pupil.

One method for practising this invention includes premarking of the cornea with a corneal marking device of approximately the same size as the multiple lens system to be affixed to the eye. After the cornea is so marked, the lens is inserted under the marker. The marker should be of sufficient dimension to mark the cornea sufficiently superior to the natural pupil to insure that the multiple lens system to be located in the altered pupil will be located at Lhe desired location in the altered pupil. Thereafter, the pupil can be further altered as desired using the selected technique to allow entrance of light into the posterior segment of the eye from the near lens system located superior to the natural pupil.

It is also envisioned that the artificial lens implanted into the eye having an altered natural pupil (either an accessory pupil or enlarged pupil) may be a multiple optical system having two identical optical or lens systems in an eccentric arrangement. The superiorly positioned optical system is adapted to be preferably located in the altered portion of the pupil and the second optical system would be located in the natural pupil.

As such, the above described method has specific utility for altering the size and/or shape of a natural pupil to accommodate an artificial lens having a near lens located superiorly to direct light rays to a macula including specifically, but without limitation, the artificial lens described herein.

By utilizing the teaching of the present invention, the preferred embodiment uses prisms within the eccentrically arranged lens system to create light rays for disparate macular images which are directed onto the macula of the retina by the lens system at any given time while concurrently diverting blurred or otherwise uninterruptable light rays of the images to a location which is at least one of inferior to or superior to the macula. Also, the positioning of the lens system within the pupillary zone may allow for a partial or a complete elimination of one of the optical systems by adjacent structures such as the eyelids and/or eyelashes. Several examples are shown herein including, for example, the illustrations in FIGS. 3 and 16.

Thus, the use of a prism in the optical systems for near vision optically separates the light rays of the distant lens system of the optical systems in the intraocular lens or other artificial lens. The use of a prism creates disparity of the highest order by producing two completely different light ray paths from eccentric lens system. This is different than simultaneous vision which is produced by two almost identical images (difference in size) of the same object passed by concentric lens systems. Eccentricity without prisms also creates two almost identical images by creates the possibility of covering one of the lens systems with eyelids or eyelashes.

The use of a prism in the optical system for far vision optically separates light rays for the retinal images of the optical systems in the same manner thereby creating a disparity of the highest order in the form of two completely different retinal images from different objects.

It is envisioned that the artificial lens of the present invention can be incorporated into an optical lens system having a lens body wherein the lens body including the imaging systems are implanted onto the cornea or intracorneal of the eye and are formed of a on-lay material which is compatible with the epithelial cells growing thereacross to implant the optical lens systems in a subepithelial location.

By utilizing certain teachings of the present invention, it is possible to make an extremely small intraocular lens which can be folded or manipulated in such a manner that the same can be passed through a very small incision in the eye and implanted into the anterior or posterior chamber of the eye through the small incision.

Further, by proper training of the patient or user, the user can utilize the eyelid motion to minimize or eliminate use of one of the lens systems as desired. As a result, the retina would be able to dark adapt more easily and thereby become more sensitive to the available light.

The artificial lens illustrated herein utilizes several discreet lens systems elements to define each of the imaging systems. However, using known techniques, the lens systems could be molded to be an integral artificial lens. Composite lens system having a predetermined shape so that the same can be positioned within the eye. For example, the lens system could be molded to form the extended objective lens as illustrated in FIG. 18 by using known techniques such that the lens of form integral with the lens body. Various types of material having different selected angles of incident and angles of refraction could be utilized for the lens system.

As discussed in connection with the description of FIGS. 13, 14 and 15 hereinbefore, the pupil of the eye is altered and configured into preferably a generally elongated vertically extending elliptical shape. The alteration and reconstruction of the pupil can be formed in one of two ways. The pupil alteration can have its size, shape, position or configuration altered (which is covered generically by the word "altered" as used herein) to improve or perfect the optical systems by performing a surgical alteration, such as an iridectomy. The surgical alteration would be accomplished in the usual way for performing intraocular surgery. This could involve either a sphincterotomy or excision of a portion of iris to form an accessory pupil.

Also, the alteration could be formed with a laser. An Argon laser could be utilized to cause contraction of the iris tissue peripheral to the pupil resulting in vertical oval shaped pupil.

Another type of laser that can be utilized for performing a laser alteration is a Yag laser. By utilizing a Yag laser, the laser beam actually cuts the iris sphincter, thereby enlarging the overall size as well as configuration of the pupil. This allows for selectively enlarging the pupil the one direction, but not significantly shifting the overall pupil. By utilizing the amount of tissue actually cut by the Yag laser, the pupil size can be determined.

Another surgical step that could be utilized is that the recipient's cornea could be marked with a marking ring to assure proper location of the artificial lens within the stroma.

By marking the cornea surface with an indentation ring, the cornea can be precisely marked to divide the optical zone of the cornea such that one portion of the optical zone can be used for the near focus optical system while the other portion is to be used for the distance focusing system.

In the present invention, when an image is directed onto the retina at a location superior of the macula, the brain perceives the image as in the down position. The user would spontaneously turn the eye downward to look through the near lens system. This movement would "tuck" the distant lens system behind the lower lid.

In the alternative, when an image is directed onto the retina at a location inferior to the macula as would be the case in the distance lens system with the base down prism, the brain perceives the image as in the up position. The user would spontaneously turn the eye upward to look through the distant lens system and the upward movement would "tuck" the near lens system behind the upper lid.

Using these characteristics, the artificial lens can be specifically designed for a patient's special requirements. The typical dimension of an artificial lens would be in the range of 5 mm to 6 mm diameter, also, the lens could be oblong with a minor diameter of about 3.5 mm to about 4 mm and a major diameter of about 6 mm.

Also, the distant lens could have a diameter of about 5 mm to 6 mm with the near lens being smaller, say in the order of 2 mm to 3 mm and be located superiorly in the distant lens in an eccentric relationship.

An intraocular lens could have the central body functioning as the distant lens system with a diameter in the order of 3.5 mm and the near lens system in an eccentric arrangement having a diameter of about 1.5 mm to about 2.0 mm located superiorly in the lens body.

Materials used in artificial lens for producing this invention require a high index of refraction to obtain the plus power in the lens for near vision. The curvature of the front surface of the cornea could be changed to obtain more plus power. Changing the curvature of the front surface of the cornea is an alternate method that could be used to effect more plus power.

Suitable materials would include those materials that are bio-compatible and which do have a high index of refraction, examples of such material are Polysulfone, Polycarbonate, Fluorinated Silicone-PMMA Lens combination and other suitable bio-compatible materials.

What is claimed is:

1. An artificial lens system adapted for use in an eye having a macula comprising a first optical lens system and second optical lens system wherein the principal axis of each optical lens system is eccentric to each other for directing light rays from each image of each of the first optical lens system and the second optical lens system onto a macula of an eye, and wherein the first optical lens system has a predetermined diopter power for receiving light rays from a near object, further including a prism having a preselected diopter power, said prism being positioned on a selected surface of said first optical lens system for directing a portion of the light rays from the near object onto a macula of an eye and the light rays of a different object superior of the macula.

2. The artificial lens system of claim 1 wherein the second optical lens system includes an optical member which is adapted to produce disparate near and distant macular images.

3. The artificial lens system of claim 1 wherein said first optical lens system and said second optical lens system each have a proximal edge which are positioned adjacent to each other and wherein said prism includes a base and a wedged-shaped edge wherein said prism is positioned with said wedged-shaped edge located adjacent the proximal edge of said first optical lens system.

4. The artificial lens system of claim 1 wherein said first optical lens system and said second optical lens system each have a proximal edge which are positioned adjacent to each other and wherein said second optical lens system includes a second prism having a base and a wedge-shaped edge and wherein said second prism is positioned with said wedge-shaped edge located adjacent the proximal edge of said second optical lens system.

5. The artificial lens system of claim 1 wherein said first optical lens system has a predetermined diopter power for receiving and directing light rays from an object onto a macula of an eye; and said second optical lens system has a predetermined diopter power and wherein said second optical lens system is positioned inferior of said first optical lens system for receiving and directing light rays from the same object onto a macula of an eye.

6. The artificial lens system of claim 5 wherein said prism has a predetermined diopter power, said prism being positioned on a selected surface of said first optical lens system for directing selected paracentral light rays from a near object onto a macula of an eye and central rays directed superior to the macula.

7. The artificial lens system of claim 6 further excluding a second prism having a predetermined diopter power, said prism being positioned on a selected surface of said second optical lens system for directing selected paracentral light rays from a distant object onto a macula of an eye with the central light rays inferior to the macula.

8. An artificial lens system adapted for use in an eye comprising means adapted to be affixed to an eye for producing disparate near and distant macular images, said image producing means including a first lens having a predetermined diopter power for receiving light rays from a near object; and a first prism having a preselected diopter power, said first prism being positioned on a selected surface of said first lens for directing paracentral light rays from a near object onto a macula of an eye and central light rays from a near object superior of the macula.

9. The artificial lens systems of claim 8 further comprising a second lens having a predetermined diopter power positioned inferior of said first lens for receiving light rays from a distant object; and a second prism having a preselected diopter power, said second prism being positioned on a selected surface of said second lens for directing paracentral light rays from a distant object onto a macula of an eye and the central light rays from a distant object inferior of the macula.

10. The artificial lens system of claim 8 wherein said first lens of said image producing means has a predetermined diopter power for receiving light rays from a near object, said first lens including means for defining an anterior lens surface and a posterior lens surface;

said image producing means further including a second lens spaced from said first lens and having a second predetermined diopter power said second lens being positioned inferior to the first lens for receiving light rays from a distant object, said second lens including means for defining a second anterior lens surface and a second posterior lens surface; and a second prism having a second preselected diopter power, said second prism being positioned contiguous the second posterior lens surface of said second lens for directing paracentral light rays from a distant object onto the macula of the eye and central light rays from a distant object inferior of the macula.

11. The artificial lens systems of claim 8 wherein said first lens and said first prism affixed thereto define a corneal overlay lens adapted to be affixed onto the cornea of an eye.

12. The artificial lens systems of claim 8 wherein said first lens and said first prism affixed thereto define a corneal-stroma lens adapted to be implanted into a cornea of an eye.

13. The artificial lens system of claim 8 wherein said first lens includes an edge and wherein said first prism includes a base and a wedged-shaped edge and wherein said first prism is positioned with said wedged-shaped edge located adjacent the edge of said first lens.

14. The artificial lens system of claim 8 wherein said first lens includes a proximal edge and wherein said first lens includes a first prism having a base and a wedge-shaped edge and wherein said first prism is positioned with said wedge shaped edge located adjacent the proximal edge of said first lens.

15. The artificial lens systems of claim 10 wherein said first lens and said first prism affixed thereto and said second lens and said second prism affixed thereto define a corneal overlay lens adapted to be affixed onto the cornea of an eye.

16. The artificial lens systems of claim 10 wherein said first lens and said first prism affixed thereto and said second lens and said second prism affixed thereto define an corneal-stroma lens adapted to be implanted into a cornea of an eye.

17. The artificial lens systems of claim 10 wherein said first lens and said first prism affixed thereto and said second lens and said second prism affixed thereto define a lens body of an intraocular lens.

18. The artificial lens systems of claim 17 further comprising:

resilient support means operatively connected to said lens body to define an intraocular lens.

19. The artificial lens systems of claim 18 wherein said lens body has an outer peripheral surface for supporting said resilient support means.

20. The artificial lens systems of claim 19 wherein resilient support means comprises two haptic members equally spaced around said outer peripheral surface and in a plane substantially coplanar with the lens body.

21. The artificial lens systems of claim 20 wherein said resilient support means comprises three haptic members equally spaced around said outer peripheral surface and in a plane substantially coplanar with the lens body.

22. An artificial lens system adapted for use in an eye having a macula comprising means adapted to be affixed to an eye having a first optical lens system and second optical lens system wherein the principal axis of each optical lens system is eccentric to each other for directing light rays from each image of each of the first optical lens system and second optical lens system onto a macula of an eye, said first optical lens system and second optical lens system being adapted to produce at least one of disparate near and distant macular images of an object and two similar images of an object wherein at least a portion of light rays from each image is directed upon a macula of an eye and wherein each of said first optical lens system and second optical lens system respectively include, a first and second prism for passing different light rays from an object.

23. The artificial lens system of claim 22 wherein the and first prism is adapted to direct the selected paracentral light rays from each object onto the macula of an eye and central light ray from a different object to at least one of a preselected location superior to the macula and a preselected location inferior to the macula.

24. An artificial lens system adapted to be located in an eye having a macula comprising:

a first lens system for receiving and directing light rays from a near object; and a second lens system positioned inferior in an eccentric arrangement to the first lens system for receiving and directing light rays from a distant object; and wherein at least one of said first lens system and second lens system includes a prism for passing light rays from its applicable object onto the macula of an eye and to at least one of a location inferior and superior of the macula.

25. An optical lens system for a human eye having a macula comprising a lens body having an anterior surface and a posterior surface, said lens body including first and second optical eccentrically arranged lens systems for forming at least two images of an object which are adapted to be transmitted from the anterior surface of the lens body, through the lens body and beyond the posterior surface of the lens, each of said optical lens system including means for directing selected paracentral light rays from each object onto a macula, of an eye and central light rays from each object being directed to at least one of superior to and inferior to the macula of the eye in a manner to obtain an optical effect for substitution of the loss of accommodation of an eye and wherein each of said optical lens systems includes a prism for passing different light rays from an object.

26. The optical lens systems of claim 25 wherein said means for directing said selected paracentral light rays directs rays from each of different objects onto the macula.

* * * * *